United States Patent [19]

Bright et al.

[11] Patent Number: 5,750,756
[45] Date of Patent: May 12, 1998

[54] PROCESS FOR THE FORMATION OF HYDROCARBYL BIS(HYDROCARBYL PHOSPHATE)

[75] Inventors: Danielle A. Bright, New City; Ronald L. Pirrelli, Mahopac, both of N.Y.

[73] Assignee: Akzo Nobel nv, Arnhem, Netherlands

[21] Appl. No.: 681,735

[22] Filed: Jul. 29, 1996

Related U.S. Application Data

[63] Continuation-in-part of Ser. No. 332,671, Nov. 1, 1994.
[51] Int. Cl.$^6$ ........................................... C07F 9/12
[52] U.S. Cl. ........................................... 558/162
[58] Field of Search ........................................... 558/162

[56] References Cited

U.S. PATENT DOCUMENTS

| | | | |
|---|---|---|---|
| 3,254,973 | 6/1966 | Giammaria et al. | 44/69 |
| 3,642,959 | 2/1972 | Nichols | 558/99 |
| 4,133,846 | 1/1979 | Albright | 260/928 |
| 4,343,732 | 8/1982 | Zama et al. | 524/114 |
| 5,122,556 | 6/1992 | Kambour | 524/141 |
| 5,457,221 | 10/1995 | Brady et al. | 558/99 |

FOREIGN PATENT DOCUMENTS

| | | | |
|---|---|---|---|
| 509506 | 10/1992 | European Pat. Off. | C07F 9/12 |
| 521628 | 1/1993 | European Pat. Off. | C07F 9/12 |
| 227632 | 9/1988 | Japan | C08G 79/04 |

OTHER PUBLICATIONS

Derwent Patent Abstract 05192 J/49 (1982), abstracting Japanese Patent Publication No. 57/174,331.

*Primary Examiner*—Michael G. Ambrose
*Attorney, Agent, or Firm*—Richard P. Fennelly; Louis A. Morris

[57] ABSTRACT

A process for forming a composition containing over, for example, about 90% by weight of an alkylene-arylene bridging group-containing bis(diphenyl phosphate) compound and less than, for example, 10%, by weight, of monophosphate by-product. This process involves the reaction of a composition containing a diphenyl halophosphate and an alkylene-arylene bridging group-containing diol, in the presence of a catalytic amount of a Lewis acid catalyst, utilizing a means, during the course of the reaction, for removal of hydrohalide by-product. The preferred means that are used for removal of hydrohalide by-product include:

performing the reaction in a hydrocarbon solvent;
utilizing vacuum to remove such by-product;
utilizing sparging with an inert gas; and
compatible combinations of one or more of the foregoing means.

11 Claims, No Drawings

PROCESS FOR THE FORMATION OF HYDROCARBYL BIS(HYDROCARBYL PHOSPHATE)

This is a continuation-in-part of U.S. Ser. No. 08/332,671, filed Nov. 1, 1994.

BACKGROUND OF THE INVENTION

Processes for the synthesis of a hydrocarbyl bis (dihydrocarbyl phosphate) by the reaction of a hydrocarbyl diol with a dihydrocarbyl halophosphate in the presence of a Lewis acid catalyst are known to the prior art. For example, U.S. Pat. No. 3,254,973 to J. J. Giammaria et al. illustrates such a general reaction beginning at Col. 6, line 20 but teaches the use of nitrogen gas to remove hydrohalide by-product at the end of the reaction, rather than during the course of the actual reaction itself while the product composition is being formed. This patent does not discuss anything about the purity of the product that is formed by its technique. U.S. Pat. No. 4,133,846 to J. A. Albright illustrates an analogous reaction, does not show the nitrogen sparge aspect, and merely suggests (at Col. 4, lines 45–47) that an organic solvent can be used during the reaction without any description of an advantage for doing so. It too is silent in regard to the product purity as compared to one made without nitrogen sparging, for example, and its Examples fail to show either the use of solvent or nitrogen sparging. More recent U.S. Pat. No. 4,343,732 to T. Zama et al. shows the reaction of certain diols, phosphorus oxychloride, and certain alcohols and phenols, in the presence of aluminum chloride as a catalyst, indicates (at Col. 4, lines 21–22) that inert solvents, such as toluene and xylene, may be used, but also describes no advantage for the use of a solvent in its particular process.

It has been unexpectedly been found that when the aforementioned type of process is practiced without substantially concurrent means to remove hydrohalide by-product, the product that is formed has a lower assay and contains a greater degree of undesired monophosphate by-product, such as triphenyl phosphate and isopropenyl phenyl diphenyl phosphate as well as other impurities from product breakdown.

SUMMARY OF THE INVENTION

The present invention, in one embodiment, relates to a process for forming a composition containing more bisphosphate and less undesired monophosphate by-product with the desired alkylene-arylene bridging group-containing bis (diphenyl phosphate) compound, which is normally prone to be formed with such monophosphate by-product formation. The instant process comprises the reaction of a composition consisting essentially of diaryl halophosphate and an alkylene-arylene bridging group-containing diol, in the presence of a catalytic amount of a Lewis acid catalyst, utilizing a means, during the reaction, for removal of hydrohalide by-product selected from the group consisting of:

performing the reaction in a hydrocarbon solvent;

utilizing vacuum to remove such by-product; and a combination of performing the reaction in a hydrocarbon solvent and utilizing vacuum to remove such by product.

The present invention, in another embodiment thereof, relates to an alkylene-arylene bridging group-containing bis(diphenyl phosphate) composition, normally prone to be formed with undesired monophosphate by-product, which composition is formed from the reaction of a diaryl halophosphate and an alkylene-arylene bridging group-containing diol, as previously described. This desired composition contains more than 85% by weight of bisphosphate and less than 10%, by weight, of undesired monophosphate by-products.

DETAILED DESCRIPTION OF THE INVENTION

The present process is one which is intended to synthesize a hydrocarbyl bisphosphate composition containing containing more bisphosphate (preferably over 85%, most preferably over 90%) and less undesired monophosphate by-product (preferably less than 15%, most preferably less than 10%), with the desired hydrocarbyl bisphosphate compound which is of the following formula:

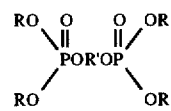

where R can be hydrocarbyl (such as, substituted or unsubstituted aryl, e.g., phenyl) and R' is an alkylene-arylene bridging group, of the general formula —Ar—R"—Ar—, where Ar is arylene, such as phenylene and R" is alkylene. Representative diols of this type can be represented by Bisphenol A. Conventional processes for forming such compounds result in the formation of undesired monophosphate by-products, such as triphenyl phosphate and/or isopropenyl phenyl diphenyl phosphate, above the levels claimed herein due to the nature of the bridging group R', and a lower assay product.

The dihydrocarbyl halophosphate reactant used in the instant process has the formula

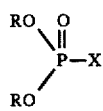

where R is hydrocarbyl (e.g., substituted or unsubstituted aryl, such as phenyl) and X is halogen. Preferred compounds are the diarylchlorophosphates (e.g., diphenylchlorophosphate). This reactant is preferably present at about 2:1 (on a molar basis) to the following dihydroxy reaction.

The dihydroxy reactant (HOR'OH) is used to form the bridging group R' in the final compounds. The reaction is run at elevated temperature (above about 20° C.) using an effective amount (e.g., about 0.01% to about 1% based upon the weight of the selected dihydrocarbyl halophosphate reagent) of a Lewis acid catalyst. Such catalysts include such transition metal halides as magnesium chloride, aluminum chloride, zinc chloride, titanium tetrachloride and the like.

The present invention, in one embodiment, relies upon the presence of an additional amount of a liquid hydrocarbon, for example, an aliphatic hydrocarbon, such as heptane, or an aromatic solvent, such as toluene, to assist, as a "chaser", in driving off the hydrogen halide by-product during the course of the reaction rather than after the reaction has been run as shown in U.S. Pat. No. 3,254,973 to J. J. Giammaria et al. Generally speaking, the amount of solvent that is used will be up to about 100% by weight of the weight of diol and halophosphate, preferably up to about 50%, more preferably up to about 20%. The use of this liquid hydrocarbon allows for a high purity product to be formed at lower temperatures than possible if the liquid hydrocarbon were absent.

In yet another embodiment of the invention, a suitable inert gas to the reaction, such as nitrogen, can be used to drive off the undesired product during the course of the reaction to enable production of the desired bis(phosphate) compound in the final composition.

In yet another embodiment of the invention a combination of solvent and sparging gas can be used to enable production of the desired bis(phosphate) compound in the final composition.

Finally, if desired, the use of vacuum can be used to remove the undesired hydrogen halide during the reaction.

Compatible combinations of solvent, inert gas, and vacuum techniques for the removal of the hydrogen halide by-product can be used, if desired.

The present invention is illustrated by the Examples which follow.

EXAMPLE 1

This Example illustrates an embodiment of the present invention.

Diphenyl chlorophosphate (0.5 mole), Bisphenol A (0.25 mole), magnesium chloride ($2.63 \times 10^{-3}$ mole), and heptane (20 wt %) were heated to reflux (about 99° C.) for six hours. The disappearance of the hydroxyl functionality in the Bisphenol A reagent was monitored by infrared analysis. The reaction mixture was washed with 5 wt % caustic followed by two water washes.

Liquid chromatographic analysis of the product showed the following composition: Bisphenol A bis(diphenyl phosphate), also termed "$P_2$" (92.3 wt %); the next higher oligomer "$P_3$" of the foregoing (2.4 area %); triphenyl phosphate (1.5 wt %); and isopropenylphenyl diphenyl phosphate (0.5 area %). The material solidified upon cooling and had a melting point of from about 47° C. to about 55° C.

EXAMPLE 2

The same reaction as illustrated in Example 1 was carried out under vacuum of 200 mbar to remove hydrogen chloride. The following composition was obtained:

| | |
|---|---|
| Bisphenol A bis(diphenyl phosphate) "$P_2$": | 91% by weight |
| Triphenyl phosphate: | 1.6% by weight |
| Isopropenyl phenyl diphenyl phosphate: | 4.7% by area (about 0.5 wt %) |
| Bisphenol A oligomeric(diphenyl phosphate) "$P_3$": | 2.3% by area |

The melting range of the product was 45° C.–55° C.

EXAMPLE 3

The same reaction as illustrated in Example 1 was carried out under nitrogen sparge to remove hydrogen chloride. The following composition was obtained:

| | |
|---|---|
| Bisphenol A bis(diphenyl phosphate) "$P_2$": | 90% by weight |
| Triphenyl phosphate: | 1.9% by weight |
| Isopropenyl phenyl diphenyl phosphate: | 8.5% by area (about 1 wt %) |
| Bisphenol A oligomeric(diphenyl phosphate) "$P_3$": | 2.4% by area |

The melting range of the product was 45° C.–55° C.

COMPARATIVE EXAMPLE 4

The same reaction as illustrated in Example 1 was carried out without the use of either solvent or other physical means (e.g., vacuum or nitrogen sparge) to remove hydrogen chloride by-product. The following composition was obtained:

| | |
|---|---|
| Bisphenol A bis(diphenyl phosphate) "$P_2$": | 81% by weight |
| Triphenyl phosphate: | 4.4% by weight |
| Isopropenyl phenyl diphenyl phosphate: | 14.7% by area |
| Bisphenol A oligomeric(diphenyl phosphate) "$P_3$": | 1.8% by area |

COMPARATIVE EXAMPLE 5

The same reaction as illustrated in Example 1 was carried out with nitrogen sparging at the end of the reaction, as suggested in U.S. Pat. No. 3,254,973 to J. J. Giammaria et al., rather than during the course of the reaction in accordance with the present invention The following composition was obtained:

| | |
|---|---|
| Bisphenol A bis(diphenyl phosphate) "$P_2$": | 80.4% by weight |
| Triphenyl phosphate: | 4.4% by weight |
| Isopropenyl phenyl diphenyl phosphate: | 9.8% by area |
| Bisphenol A oligomeric(diphenyl phosphate) "$P_3$": | 2.2% by area |

EXAMPLE 6

This Example illustrates the introduction of oligomers into the composition by adding monophenyl dichlorophosphate (MPCP) to the reaction mixture in order to keep it liquid.

Diphenyl chlorophosphate (588 g, 2.19 moles), monophenyl dichlorophosphate (12.0 g, 0.057 mole), Bisphenol A (262.8 g, 1.15 moles), magnesium chloride (2.5 g) and n-heptane (173.2 g, 20% by weight of reaction mixture) were heated to reflux temperature of heptane (99° C.–100° C.) and kept at that temperature for six hours. Heptane was distilled to increase the reaction temperature to 140° C. It was kept at 140° C. for an additional eight hours.

The reaction mixture was then washed at 60° C. with 1.2 liters of 2% caustic, followed by 1.2 liters of 1% caustic and 2×1.2 liters of water. After drying, there was obtained 736.4 g of a hazy liquid (94.6%) which was filtered through CELITE filter aid. The acid number was 0.011 mg KOH/g, and LC analysis gave the following results: 84:3% by wt. P2, 1.5% by wt. TPP, 0.09% by wt. phenol, 8.4% by area P3, 0.9% by area of half-ester, and 2.3% by area (0.2% by wt.) of isopropenylphenyl diphenyl phosphate.

EXAMPLE 7

In this Example, Bisphenol A is used as a reagent with a 95:5 weight ratio of diphenyl chlorophosphate (DPCP)/MPCP.

Diphenyl chlorophosphate (571 g, 2.13 moles), monophenyl dichlorophosphate (30.8g, 0.146 mole), magnesium chloride (2.5 g) and n-heptane 178.3 g (20% by wt. of reaction mixture) were heated to reflux temperature of heptane (99°–100° C.) for five hours. At the end of that time, heptane was distilled, and the reaction temperature was increased to 140° C. It was kept at 140° C. for an additional six hours.

The reaction mixture was then washed at 60° C. with 1.8 liters of 2% caustic (no layer separation with 1.2 liters), followed by 1.2 liters of 1% caustic and 2×1.2 liters of water. After drying, there are left 731.1 g (9.8%) of a hazy light yellow oil which was filtered through CELITE filter aid. The acid number was 0.02 mm KOH/g. LC analysis gave the following results: 75% by wt. P2, 1.4% by wt. TPP, 0.15% by wt. phenol, 14.7% by area P3 2.6% by area P4 and 1.8 by area (0.2% by wt.) phenol, 14.7% by area P3, 2.6% by area P4, and 1.8 by area (0.2% by wt.) of isopropenylphenyl diphenyl phosphate.

The foregoing Examples should not be construed in a limiting sense since they are intended to merely illustrate certain embodiments of the present invention. The scope of protection sought is set forth in the claims which follow.

We claim:

1. A process for forming a composition comprising an alkylene-arylene bridging group-containing bis (diaryl phosphate) compound, normally prone to monophosphate by-product formation, with the formation of more bisphosphate and less of such monophosphate by-product, which process comprises the reaction of a composition comprising diaryl halophosphate and alkylene-arylene bridging group-containing diol, in the presence of a catalytic amount of a Lewis acid catalyst, utilizing a means, substantially concurrent with the course of the reaction, for the removal of hydrohalide by-product.

2. A process as claimed in claim 1 wherein the means for the removal of hydrohalide by-product is selected from the group consisting of:

performing the reaction in a hydrocarbon solvent;

utilizing vacuum to remove such by-product;

utilizing sparging with an inert gas; and compatible combinations of one or more of the foregoing means.

3. A process as claimed in claim 1 wherein the diaryl halophosphate is diphenyl chlorophosphate.

4. A process as claimed in claim 1 wherein the diol is Bisphenol A.

5. A process as claimed in claim 1 wherein the diaryl halophosphate is diphenyl chlorophosphate and the diol is Bisphenol A.

6. A process as claimed in claim 1 wherein the Lewis acid catalyst is magnesium dichloride.

7. A process as claimed in claim 3 wherein the Lewis acid catalyst is magnesium dichloride.

8. A process as claimed in claim 4 wherein the Lewis acid catalyst is magnesium dichloride.

9. A process as claimed in claim 5 wherein the Lewis acid catalyst is magnesium dichloride.

10. A process as claimed in claim 1 wherein a hydrocarbon solvent is present at up to about 20%, by weight of the reaction medium.

11. A process as claimed in claim 10 wherein the diaryl halophosphate is diphenyl chlorophosphate, the diol is Bisphenol A, and the Lewis acid catalyst is magnesium dichloride.

* * * * *